(12) United States Patent
Bothorel et al.

(10) Patent No.: US 11,154,379 B2
(45) Date of Patent: Oct. 26, 2021

(54) METHOD FOR IMPLANT SURGERY USING AUGMENTED VISUALIZATION

(71) Applicant: TROPHY, Rochester, NY (US)

(72) Inventors: Sylvie Bothorel, Paris (FR); Philippe Maillet, Marne la Vallee (FR)

(73) Assignee: TROPHY, Croissy-Beaubourg (FR)

( * ) Notice: Subject to any disclaimer, the term of this patent is extended or adjusted under 35 U.S.C. 154(b) by 104 days.

(21) Appl. No.: 15/110,540

(22) PCT Filed: May 15, 2014

(86) PCT No.: PCT/IB2014/002021
§ 371 (c)(1),
(2) Date: Jul. 8, 2016

(87) PCT Pub. No.: WO2015/110859
PCT Pub. Date: Jul. 30, 2015

(65) Prior Publication Data
US 2016/0324598 A1 Nov. 10, 2016

Related U.S. Application Data

(60) Provisional application No. 61/929,725, filed on Jan. 21, 2014.

(51) Int. Cl.
*A61C 1/08* (2006.01)
*A61B 1/24* (2006.01)
(Continued)

(52) U.S. Cl.
CPC ............... *A61C 1/084* (2013.01); *A61B 1/24* (2013.01); *A61B 6/03* (2013.01); *A61B 6/14* (2013.01);
(Continued)

(58) Field of Classification Search
None
See application file for complete search history.

(56) References Cited

U.S. PATENT DOCUMENTS

| 6,091,546 A | 7/2000 | Spitzer |
| 7,720,191 B2 | 5/2010 | Muller |

(Continued)

FOREIGN PATENT DOCUMENTS

| WO | 2010/067267 | 6/2010 |
| WO | 2013/022544 | 2/2013 |

OTHER PUBLICATIONS

D. Katic, G. Sudra, S. Speidel, G. Castrillon-Oberndorfer, G. Eggers, and R. Dillmann, Knowledge-Based Situation Interpretation for Context-Aware Augmented Reality in Dental Implant Surgery, 2010, Proceedings of the 5th International Workshop on Medical Imaging and Augmented Reality MIAR 2010, pp. 531-540.*

(Continued)

*Primary Examiner* — Michael J Cobb

(57) ABSTRACT

A method for guiding the position of a dental drill for implant treatment of a patient, the method acquiring a volume image of patient anatomy; superimposing an image of a planned drill hole on a display of the acquired volume image according to observer instructions to form an implant plan; displaying at least a portion of the implant plan in stereoscopic form on a head-mounted device worn by an observer and tracking patient position so that the displayed portion of the implant plan is registered to the patient anatomy that lies in the observer's field of view; and highlighting the location of the planned drill hole on the head-mounted device display.

15 Claims, 18 Drawing Sheets

(51) Int. Cl.

| | |
|---|---|
| *A61B 6/00* | (2006.01) |
| *A61B 34/20* | (2016.01) |
| *A61B 90/50* | (2016.01) |
| *G02B 27/01* | (2006.01) |
| *G03B 42/02* | (2006.01) |
| *A61B 6/14* | (2006.01) |
| *A61B 6/03* | (2006.01) |
| *A61B 34/10* | (2016.01) |
| *A61B 90/00* | (2016.01) |

(52) U.S. Cl.
CPC ............ *A61B 6/5247* (2013.01); *A61B 34/20* (2016.02); *A61B 90/37* (2016.02); *A61B 90/50* (2016.02); *G02B 27/017* (2013.01); *G03B 42/026* (2013.01); *A61B 6/5229* (2013.01); *A61B 2034/104* (2016.02); *A61B 2034/107* (2016.02); *A61B 2034/2065* (2016.02); *A61B 2090/365* (2016.02); *A61B 2090/371* (2016.02); *A61B 2090/372* (2016.02); *A61B 2090/3937* (2016.02); *A61B 2090/3966* (2016.02); *A61B 2090/502* (2016.02); *G02B 2027/014* (2013.01); *G02B 2027/0134* (2013.01); *G02B 2027/0138* (2013.01); *G02B 2027/0141* (2013.01); *G02B 2027/0178* (2013.01)

(56) References Cited

U.S. PATENT DOCUMENTS

| | | | | |
|---|---|---|---|---|
| 7,804,933 | B2 | 9/2010 | Nyholm | |
| 8,172,573 | B2* | 5/2012 | Sonenfeld | A61C 1/084 433/173 |
| 8,576,276 | B2 | 11/2013 | Bar-Zeev et al. | |
| 8,582,209 | B1 | 11/2013 | Amirparviz | |
| 8,705,177 | B1* | 4/2014 | Miao | G02B 27/0172 345/8 |
| 2003/0004041 | A1 | 1/2003 | Hartman et al. | |
| 2003/0227470 | A1* | 12/2003 | Genc | G06F 3/011 345/633 |
| 2005/0203380 | A1* | 9/2005 | Sauer | G02B 7/002 600/417 |
| 2006/0184396 | A1* | 8/2006 | Dennis | G06Q 10/10 705/4 |
| 2006/0291968 | A1* | 12/2006 | Greenberg | A61C 1/084 408/202 |
| 2008/0088529 | A1* | 4/2008 | Tang | G02B 27/0172 345/8 |
| 2009/0191503 | A1* | 7/2009 | Matov | A61C 7/00 433/24 |
| 2010/0103247 | A1* | 4/2010 | Lim | G02B 27/2264 348/47 |
| 2010/0141905 | A1* | 6/2010 | Burke | G02B 27/017 353/85 |
| 2010/0149213 | A1* | 6/2010 | Navab | G02B 27/017 345/633 |
| 2013/0038510 | A1 | 2/2013 | Bin et al. | |
| 2013/0122463 | A1* | 5/2013 | Csillag | A61C 8/0089 433/173 |
| 2013/0131504 | A1* | 5/2013 | Daon | A61B 6/481 600/424 |
| 2013/0141421 | A1* | 6/2013 | Mount | G02B 27/017 345/419 |
| 2013/0278631 | A1* | 10/2013 | Border | G02B 27/017 345/633 |
| 2014/0022283 | A1* | 1/2014 | Chan | G02B 27/017 345/633 |
| 2014/0081659 | A1* | 3/2014 | Nawana | G16H 50/20 705/3 |
| 2014/0111639 | A1* | 4/2014 | Tanaka | G06T 7/0044 348/135 |
| 2014/0178832 | A1* | 6/2014 | Choi | A61C 1/084 433/27 |
| 2014/0307315 | A1* | 10/2014 | Bohn | G02B 27/0176 359/480 |
| 2017/0168296 | A1* | 6/2017 | Giwnewer | G02B 27/02 |

OTHER PUBLICATIONS

Nardy Casap, Sahar Nadel, Eyal Tarazi, and Ervin I. Weiss, Evaluation of a Navigation System for Dental Implantation as a Tool to Train Novice Dental Practitioners, 2011, Journal of Oral Maxillofacial Surgery 69(10):2548-2546 (Year: 2011).*

Eszter Somogyi-Ganss, Evaluation of the Accuracy of NaviDent, a Novel Dynamic Computer-Guided Navigation System for Placing Implants, 2013, Master's Thesis, Department of Prosthodontics, University of Toronto, Toronto, CA, (Year: 2013).*

Junchen Wang, Hideyuki Suenaga, Kazuto Hoshi, Liangjing Yang, Etsuko Kobayashi, Ichiro Sakuma, and Hongen Liao, Augmented Reality Navigation With Automatic Marker-Free Image Registration Using 3-D Image Overlay for Dental Surgery, Apr. 2014, IEEE Transactions on Biomedical Engineering, 61(4):1295-1304 (Year: 2014).*

International Search Report, International application No. PCT/IB2014/002021, dated Jan. 8, 2015, 2 pages.

* cited by examiner

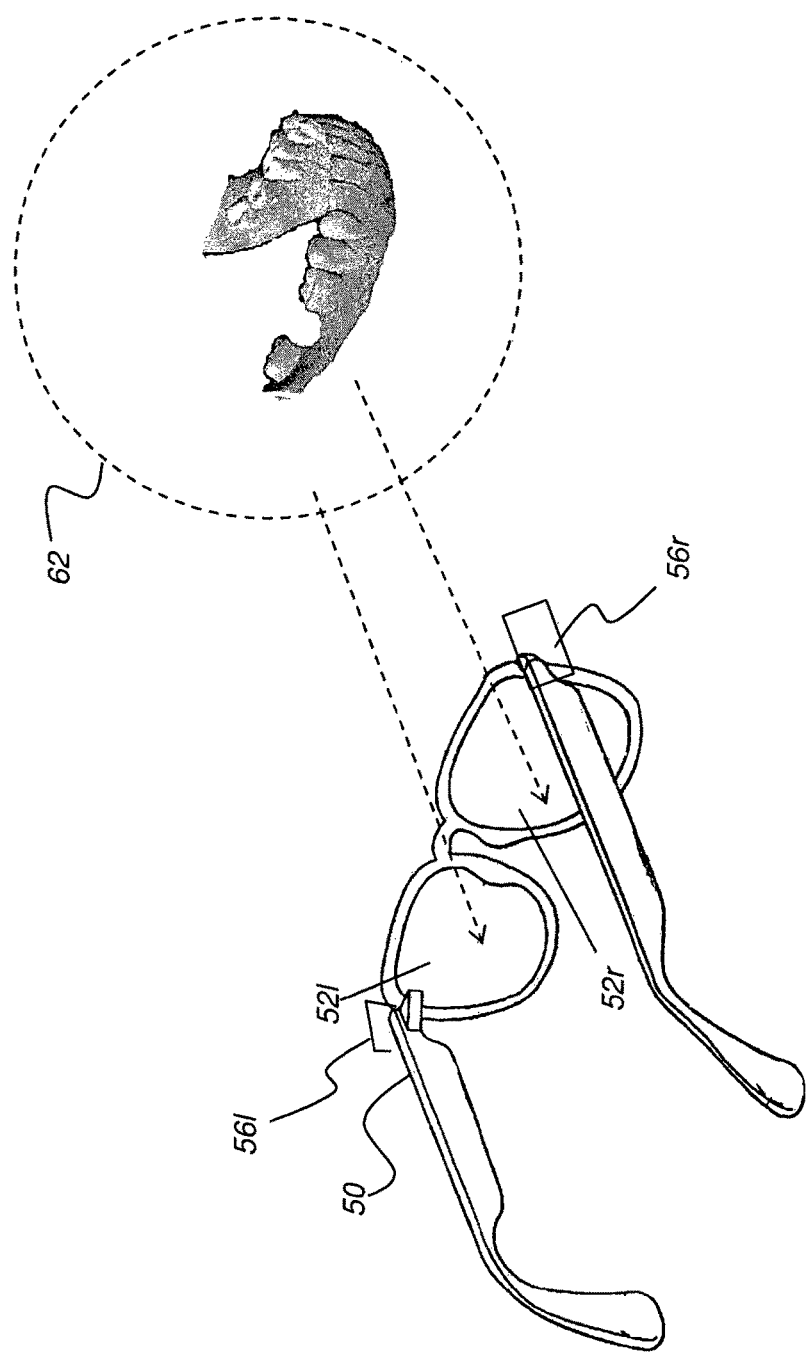

METHOD FOR IMPLANT SURGERY USING AUGMENTED VISUALIZATION

CROSS REFERENCE TO RELATED APPLICATIONS

This application claims the benefit of and is a U.S. National Phase filing of PCT Application PCT/IB14/02021 filed May 15, 2014 entitled "METHOD FOR IMPLANT SURGERY USING AUGMENTED VISUALIZATION", in the name of Bothorel et al, which itself claims the benefit of U.S. provisional application U.S. Ser. No. 61/929725 filed on Jan. 21, 2014 entitled "METHOD FOR IMPLANT SURGERY USING AUGMENTED VISUALIZATION", all of which are incorporated herein in their entirety.

TECHNICAL FIELD

The disclosure relates generally to the field of medical imaging and more particularly relates to apparatus and methods for supporting implant surgery with 3-D imaging.

BACKGROUND

Dental implants are used to replace missing or badly damaged teeth. In order to mount a dental implant securely in bony tissue, a hole is drilled into the mandibular or jaw-bone of the patient. The implant portion or abutment that holds the artificial tooth is usually made of titanium or a titanium alloy and must be able to rapidly integrate with the bone of the patient. Once the implant is seated and secure, the artificial tooth can be installed. The abutment between the implant and the prosthesis can include an elbow so that the axis of insertion of the prosthesis does not necessarily coincide with the axis of insertion of the prosthesis.

Osteotomy, that is the drilling of a hole in the jaw or mandibular bone at the proper angle and dimension, requires accuracy so that the implant fits correctly without damage to surrounding tissue or structures and so that the completed work is aesthetically acceptable. For edentulous or at least partially edentulous patients, implant planning is carefully executed. Based on information from x-ray or computerized tomography (CT) imaging of the patient's dental arch, dedicated software tools allow the dentist to define the location, diameter, length or drill depth, shape and angulation of the implant to be affixed on the patient's jawbone. One consideration in this planning is reducing the risk of damage to nearby nerves or blood vessels.

A step of the implantology process is acquiring sufficient information related to the dental clinical situation of the patient. For this purpose, a Cone Beam Computerized Tomography (CBCT) scan can be performed on the patient's dentition and a three dimensional scan of the jaw bone is obtained. The image is particularly helpful to determine the position of teeth, roots, sinus, blood vessels and nerves as well as the thickness of the bones. Depending on this anatomical information, implant planning can begin. This planning includes defining the position, diameter, length, and tilt of the implant to be screwed into the jaw bone. Among planning considerations is bone health and robustness; the implant must be screwed into bone that is sufficiently thick and strong enough to be drilled and to support the effort of chewing after the prosthesis is installed. A hole is then virtually defined on the three-dimensional image of the patient's anatomy.

The so-called standard double scan protocol is a method used to define the implant planning. A radiographic guide, defined based on a mould of the patient's mouth, is manufactured, such as using a rapid prototyping process. This guide generally includes some prosthetic teeth that are missing in the patient's mouth, some grooves and gaps that surround, existing teeth and some radio-opaque markers. A first CBCT scan of the guide is performed, along with a second CBCT scan of the patient's jaw with the guide in the patient's mouth. By registering the markers on both 3D images, the volume images can be merged and a 3D image featuring the prosthesis in the patient's mouth is obtained. The implant planning is then performed using the combined image data.

Once the drill hole is defined, in terms of length, diameter, tilt, and location, the results of implant planning, representing the hole in the 3D image of the patient's jaw, are sent to a laboratory to manufacture a surgical guide. Custom-fabricated for each patient, shaped to conform to at least a portion of the patient's dental arch, the surgical guide is fitted to the patient's mouth and includes one or more guide holes to guide the dental drill down into the jawbone according to the implant planning. The surgical guide generally has the form of a template worn in the patient's mouth and provided with at least one hole filed with a metallic sleeve and having geometric characteristics related to the holes defined in the implant planning. The laboratory sends the manufactured surgical guide to the dentist for use in the implant procedure.

At the start of surgery, the surgical guide is positioned in the patient's mouth. The dentist inserts the drilling tool into the metallic sleeve of the hole in the surgical guide and the tool is guided for drilling into the patient's jaw and jawbone. The implant can then be screwed into the bone.

There are a number of drawbacks to the existing process for implant preparation and execution. Fabrication of the surgical guide is complex and time-consuming, so that the guide can be fairly costly, with a number of workflow steps that must be carefully and correctly executed. Although some dentists are equipped with a milling machine that enables them to mill the surgical guide on-site, many dentists do not have in-house milling equipment and must work with a laboratory to manufacture the guide. It would be advantageous for saved time and cost to reduce the requirements for guide accuracy or to eliminate the need for the surgical guide altogether.

There are other practical difficulties to the surgery process, even where advanced CBCT scans and a precision fabricated surgical guide are used. During the drill placement and drilling procedure, the practitioner cannot simultaneously view the implant plan on the display while working on the patient. The need for constant reference back to the displayed implant plan interrupts the process and can contribute to errors, even causing misalignment or other problems.

Thus, it can be appreciated that there is a need for solutions that reduce the cost and complexity of implant surgery and improve the visualization of the dental practitioner for developing and implementing an implant plan.

SUMMARY

An object of the present disclosure is to advance the art of dental imaging for implant surgery. Among other aspects, embodiments of the present disclosure process and display images obtained from volume image data and modified to show dental implant planning. Embodiments of the present disclosure can reduce or eliminate the need to form a surgical guide for implant procedure in some cases, helping to save time and reduce the cost of implant surgery.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided a method for guiding the position of a dental drill for implant treatment of a patient, the method comprising: acquiring a volume image of patient anatomy; superimposing an image of a planned drill hole on a display of the acquired volume image according to observer instructions to form an implant plan; displaying at least a portion of the implant plan in stereoscopic form on a head-mounted device worn by an observer and tracking patient position so that the displayed portion of the implant plan is registered to the patient anatomy that lies in the observer's field of view; and highlighting the location of the planned drill hole on the head-mounted device display.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 6A is a schematic view that shows viewing an object in the field of view using a head-mounted device.

DETAILED DESCRIPTION OF THE EMBODIMENTS

Figure 1:
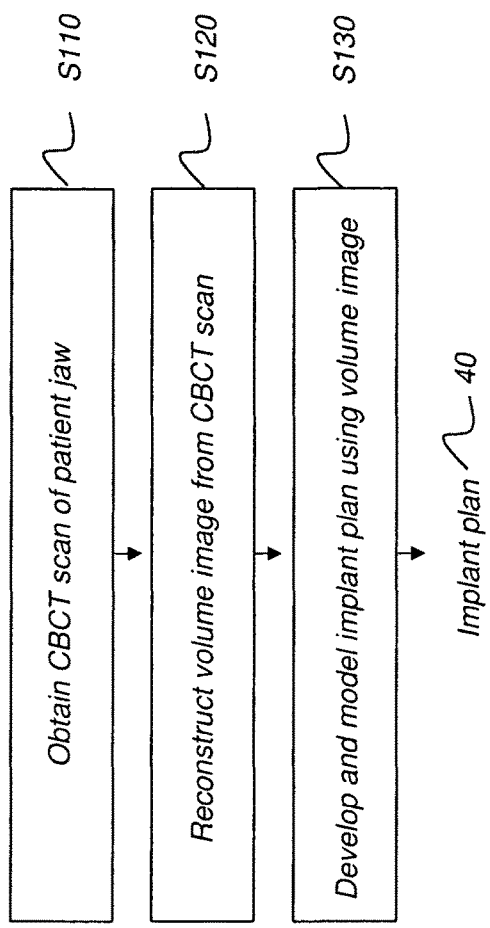
FIG. 1 is a logic flow diagram that shows steps for generating a 3-D implant plan.

The following is a detailed description of the preferred embodiments, reference being made to the drawings in which the same reference numerals identify the same elements of structure in each of the several figures.

The terms "first", "second", and so on, do not necessarily denote any ordinal, sequential, or priority relation, but are used to distinguish one step, element, or set of elements from another, unless specified otherwise.

The term "volume image" is synonymous with the terms "3-Dimensional image" or "3-D image".

The terms "viewer", "observer", "user", and "viewing practitioner" have equivalent meaning and refer generally to the practitioner or technician who views displayed, computer-generated image content.

For the image processing steps described herein, the terms "pixels" for picture image data elements, conventionally used with respect 2-D imaging and image display, and "voxels" for volume image data elements, often used with respect to 3-D imaging, can be used interchangeably. The 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, techniques described as operating upon pixels may alternately be described as operating upon the 3-D voxel data that is stored and represented in the form of 2-D pixel data for display. In the same way, techniques that operate upon voxel data can also be described as operating upon pixels.

Embodiments of the present disclosure can be used with volume data from any of a number of sources, including computed tomography (CT), CBCT, or other volume image modalities. Methods of the present disclosure generate 3-D volume data from a set of 2-D projection images.

The term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, tooth, bone, or structure, or a path from one object to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

The phrase "left-eye image" denotes the image formed by a display apparatus and intended for viewing by the left eye of the viewer. Likewise, the phrase "right-eye image" refers to the complementary image that is intended for viewing from the right eye of the viewer. The term "stereo pair" denotes the combination of right-eye image and corresponding complementary left-eye image for a stereoscopic view. A stereo pair can be hyperstereoscopic where there is an abnormally large separation distance between the angular views for the complementary left- and right-eye images, relative to the pupil-to-pupil distance of an average viewer. A stereo pair can be hypostereoscopic where there is an abnormally small separation distance between the angular views for left- and right-eye images. The separation distance is sometimes referred to as the "stereo base".

The terms "virtual view" and "virtual image" are used to connote computer-generated or computer-processed images that are displayed stereoscopically to the viewer. The virtual image that is generated can be formed by the optical system using a number of well-known techniques and this virtual image can be formed by the display optics using convergence or divergence of light.

An image is considered to be "in register" with a subject that is in the field of view when the image and subject are visually aligned from the perspective of the observer. As the term "registered" is used in the current disclosure, a registered feature of a computer-generated or virtual image is sized, positioned, and oriented on the display so that its appearance represents the planned or intended size, position, and orientation for the corresponding object, correlated to the field of view of the observer. Registration is in three dimensions, so that, from the view perspective of the practitioner/observer, the registered feature is rendered at the position and angular orientation that is appropriate for the patient who is in the treatment chair and in the visual field of the observing practitioner. Thus, for example, where the computer-generated feature is a drill hole for a patient's tooth, and where the observer is looking into the mouth of the patient, the display of the drill hole appears as if superimposed or overlaid in position within the mouth.

The logic flow diagram of FIG. 1 shows a sequence of steps for initial preparation of a 3-D implant plan using CBCT imaging, preparatory to surgery. In a scanning step S110, a set of 2-D projection images is acquired, using the scan sequence for CBCT imaging, with 2-D images of the subject obtained from multiple angles relative to the subject. The scan sequence and apparatus for CBCT imaging of a patient's jaw is described, for example, in U.S. Pat. No. 7,804,933 entitled "Dental computer tomographic imaging" to Nyholm and U.S. Pat. No. 7,720,191 entitled "Computer tomography apparatus" to Muller, both of which are incorporated herein in their entirety by reference.

In a volume reconstruction step S120, the acquired projection image data is used to generate a reconstructed 3-D volume image. This can be a standard reconstructed volume image formed from a set of 2-D projection images or may be an image generated from combined sets of 2-D projection image data, such as the fused image volume generated as described in commonly assigned U.S. 2013/0004041 entitled "Methods and Apparatus for Texture Based Filter Fusion for CBCT System and Cone-beam Image Reconstruction" by Yang et al., incorporated herein by reference in its entirety. The reconstructed volume image can then be displayed and manipulated, such as by rotation, panning, and other image manipulation utilities that are well known to those skilled in the 3-D volume image display arts.

In a plan development step S130, an implant plan 40 is developed interactively, by viewing the reconstructed image volume of the jaw at an appropriate angle, modifying the volume image by adding an image that represents an implant or drill tool device to the displayed image, and adjusting the displayed virtual implant or drill tool position within the image of the jaw until the planned implant is accurately modeled.

Procedures for interactively visualizing and adjusting the proposed location of an implant within a 3-D image of the corresponding patient anatomy are well known to those skilled in the medical and dental imaging arts. Methods for placement of a 3-D object into position relative to another 3-D object, for example, are known and widely used in computer visualization utilities.

Referring to FIG. 1, at the conclusion of step S130, implant plan 40 is formed, in which an image representing the implant or drill hole for the implant is registered within the volume image for the patient's jaw or corresponding portion of the patient's jaw to provide a virtual view that can be controlled and manipulated in 3-D space. Implant plan 40 can include additional metadata supporting the image data, with information about the patient, data on relative bone density, implant material type, hole diameter and depth, and other information.

Figure 2:
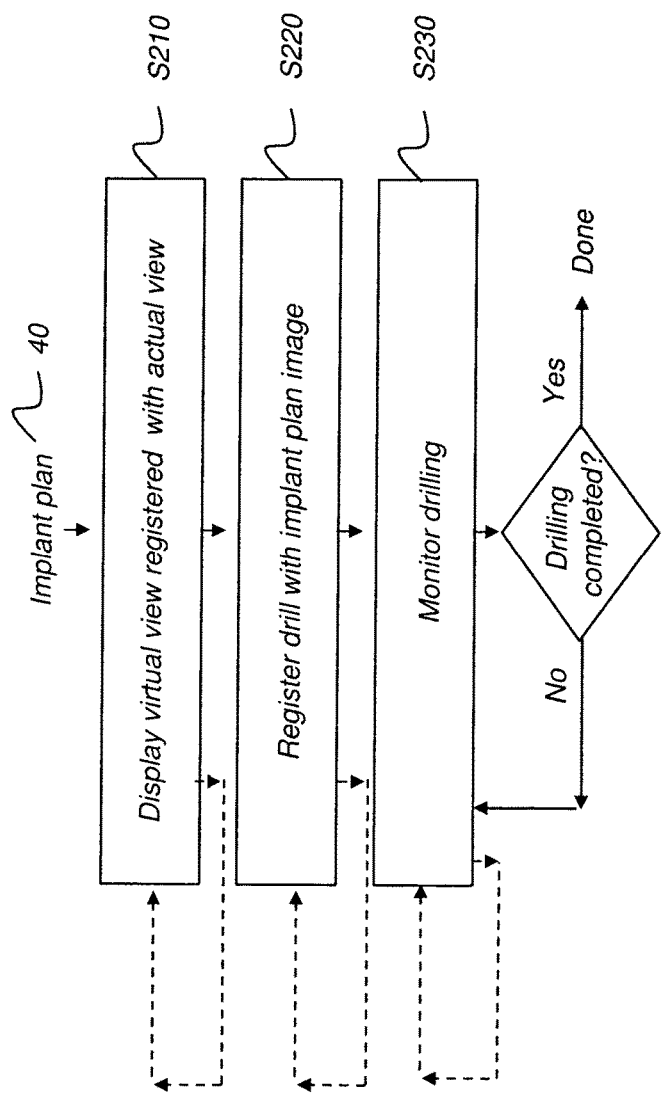
FIG. 2 is a logic flow diagram that shows steps for using a 3-D implant plan in surgery.

The logic flow diagram of FIG. 2 shows how implant plan 40, generated using the procedures of FIG. 1, is used during the surgical treatment itself. Visualization apparatus worn by the practitioner, as described in more detail subsequently, enables the modified reconstructed volume image from implant plan 40 to be viewed so that it is superimposed and registered with the corresponding jaw and teeth of the patient in the field of view of the observer. In this way, the real-world view of the actual patient seated in the treatment chair and in the visual field of the observer is effectively merged or spatially associated with the computer-generated or "virtual" view from implant plan 40, appropriately registered for scale, position, and angle.

For the sequence of FIG. 2, a visualization step S210 detects the actual view of the patient as seen by the dentist and displays, in overlaid fashion within the field of view of the dentist, the corresponding, registered virtual view. As is represented by the dashed lines shown in FIG. 2, the displayed virtual view is refreshed regularly to adjust registration, adjust view angle, and compensate for unavoidable movement or other change in position for either or both the patient and the practitioner.

A drill registration step S220, which can be executed simultaneously with step S210, registers the actual drill that is held by the dentist with the planned drill hole and related image content specified in implant plan 40. To do this, the visualization apparatus used by the practitioner detects the position of the drill in the dentist's hand and tracks this position relative to the intended drill position in implant plan 40. As is represented by the dashed lines shown in FIG. 2, the view showing drill registration is refreshed regularly to adjust registration and compensate for unavoidable movement or other change in position by either or both the patient and the practitioner.

A drill monitoring step 5230 continues to track drill progress once the drill is in position and indicates when the drilling operation is done and this phase of the surgery completed. Drill monitoring step S230 is refreshed regularly, as indicated in FIG. 2.

Figure 3A:
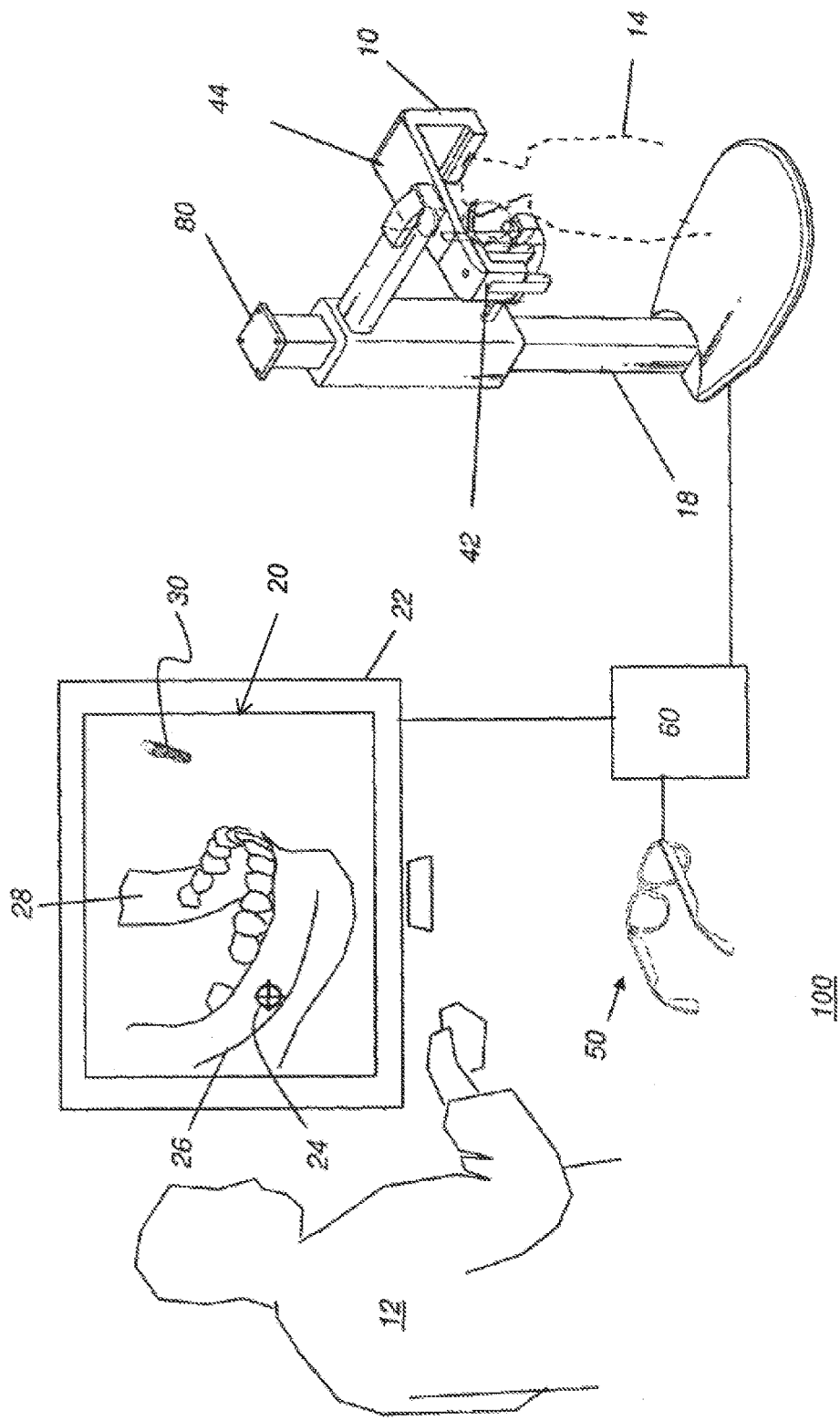
FIGS. 3A and 3B show an operator interface for generating an implant plan according to an embodiment of the present disclosure.
Figure 3B:
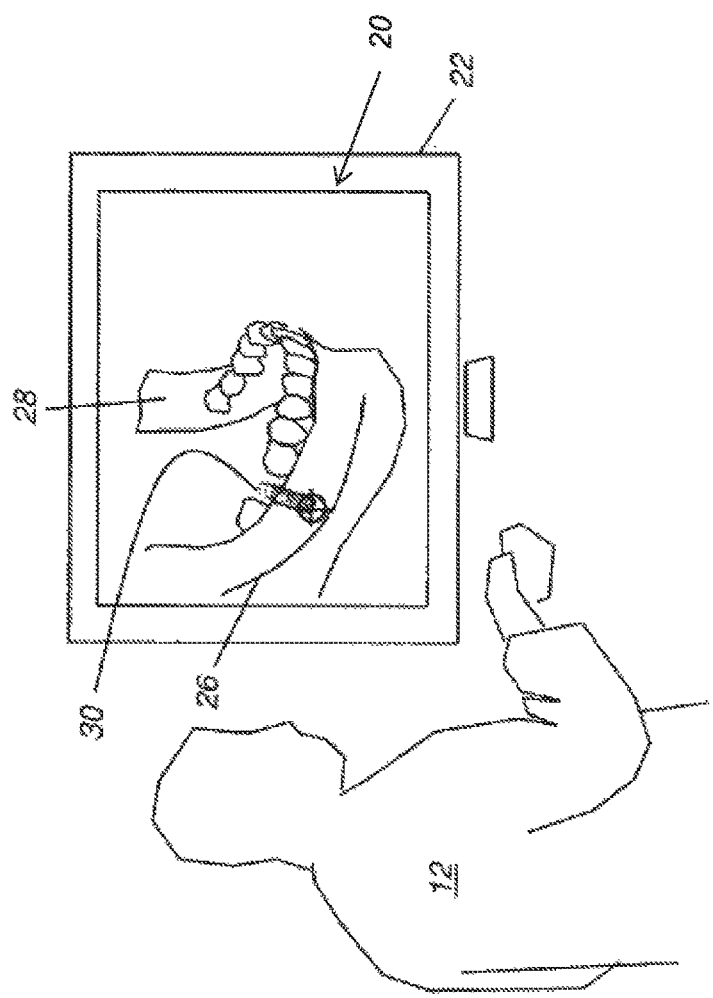

FIGS. 3A and 3B show use of an operator interface 20 for setting up an implant plan using a display 22 in a dental imaging system 100. A volume image is acquired using a cone-beam computed tomography apparatus 80 or other volume imaging system that provides 2-D image content from a number of exposure angles about the subject to a processor 60. A column 18 is adjustable for height of the subject. The patient 14, shown in dotted outline, is positioned between an x-ray source 10 and an x-ray imaging sensor panel or detector 42, also termed an imaging receiver. X-ray imaging receiver 42 rotates on a rotatable mount 44 in order to obtain a sequence of exposures. Imaging receiver 42 is positioned behind the subject, relative to x-ray source 10. With rotation of mount 44, receiver 42 and source 10 revolve about the head of the patient, typically for some portion of a full revolution. Processor 60 then generates a volume image from the individual 2-D projection images acquired by apparatus 80. The use of a head mounted device 50 for viewing stereoscopic images according to the implant plan is described in detail subsequently.

Practitioner 12 views a volume image 28 from an appropriate perspective and identifies the desired location for an implant using the display 22 and suitable operator interface utilities. In addition, practitioner 12 can also indicate other features in the volume image 28, such as a facial nerve 26 and one or more targets 24, such as the location of the top or bottom of a hole for the implant, or a central axis for drilling the hole. Operator interface 20 also displays a 3-D view of an implant 30 for placement on the displayed volume image 28. FIG. 3B shows the implant 30 in position within the volume image. The practitioner 12 is able to view the volume image from a range of suitable angles to check the angle, depth, and position of implant 30 in the plan.

Figure 4:
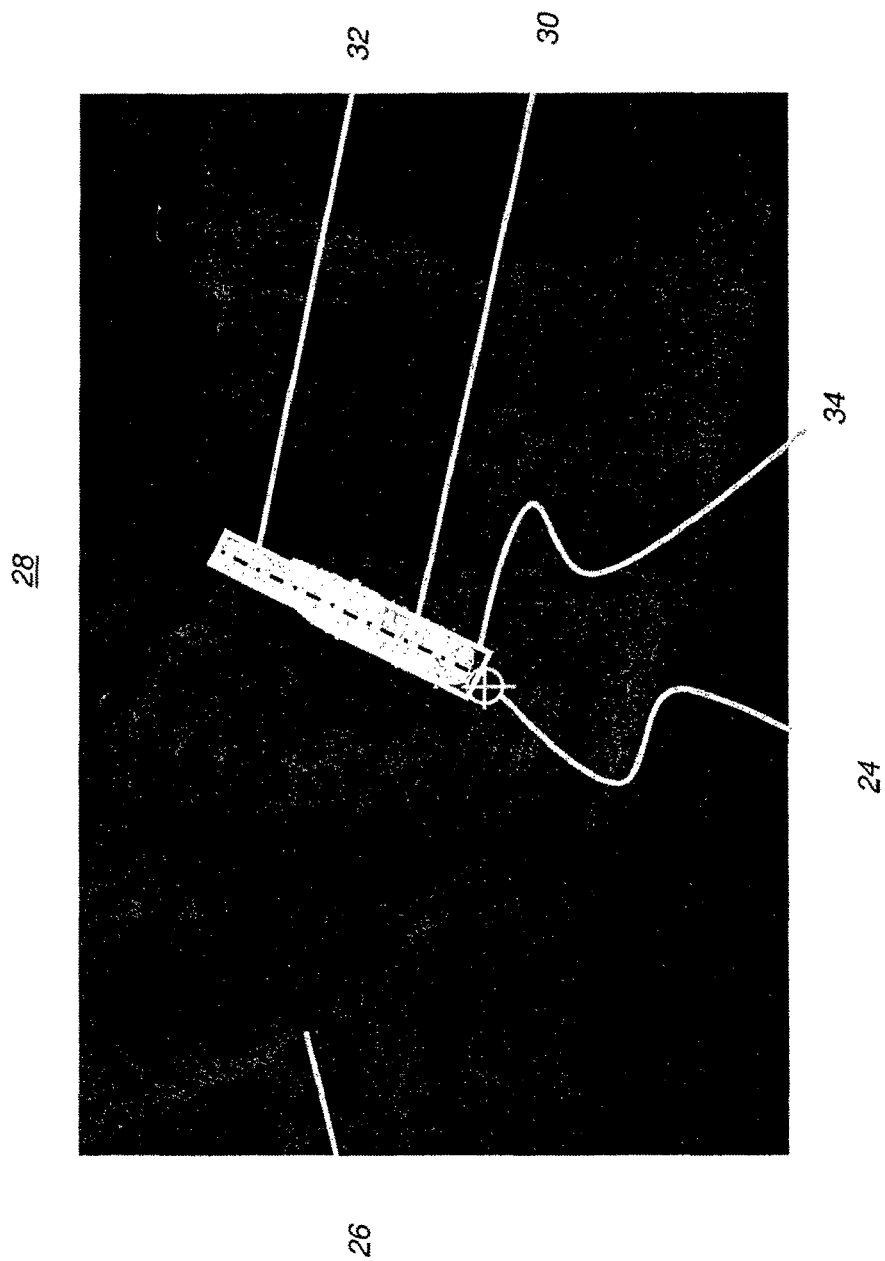
FIG. 4 is a side view that shows features of an implant plan relative to a volume image.

The side view of FIG. 4 shows placement of a proposed hole 34, drill path 32, and implant 30 for a completed implant plan. The implant plan itself is formed within the volume image so that the position of implant 30 or other feature can be viewed as a 2-D image from any suitable slice angle.

Embodiments of the present disclosure project the volume image of the implant plan in a visualization apparatus that is worn by the practitioner or otherwise disposed so that the displayed volume image is in the visual field of the practitioner and superimposed on the view of the area of the patient's mouth. The reconstructed and modified image of the implant plan appears in stereoscopic form, that is, with display of a right-eye image and a left-eye image.

Figure 5:
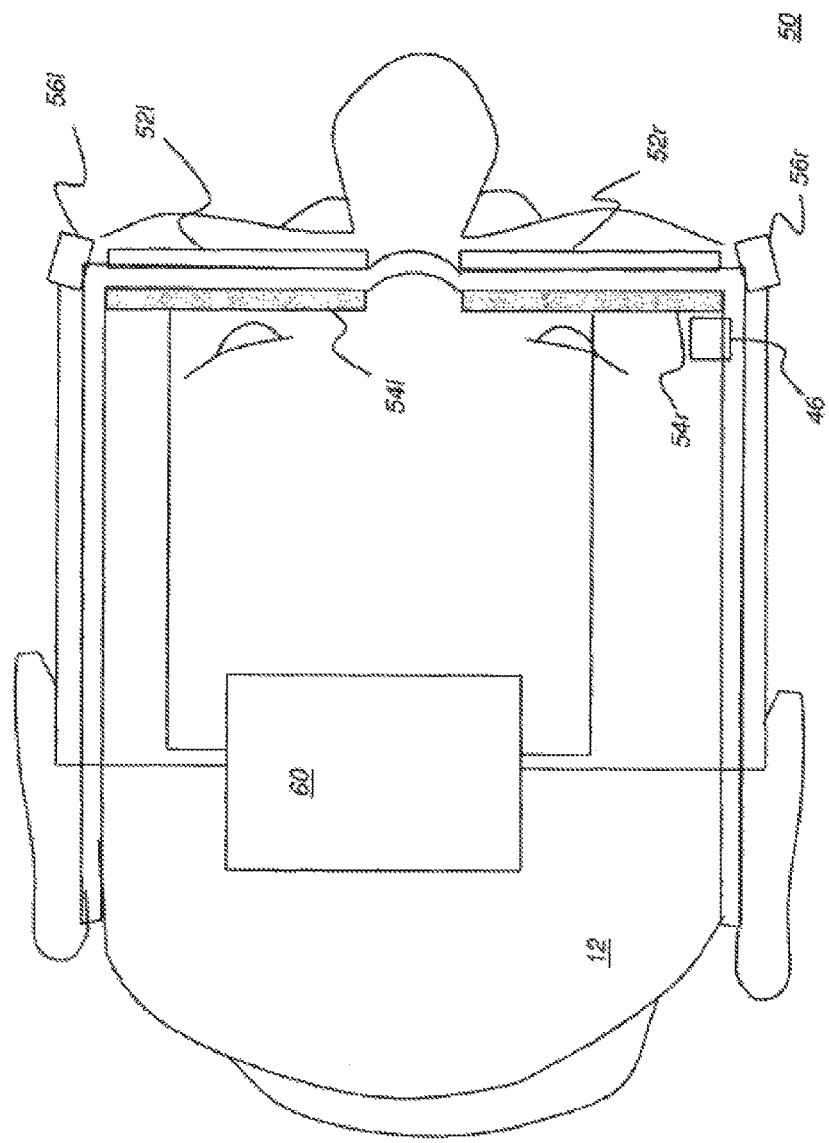
FIG. 5 is a top view schematically showing a head-mounted device in the form of eyeglasses, according to an embodiment of the present disclosure.

According to an embodiment of the present disclosure, as shown in the top view of FIG. 5, the practitioner wears a head-mounted device (HMD) 50. HMD 50 is in the form of eyeglasses or goggles. HMD 50 has a pair of transparent lenses 52*l* and 52*r* for left and right eye viewing, respectively. Lenses 52*l* and 52*r* can be corrective lenses, such as standard prescription lenses specified for the practitioner. HMD 50 also has a pair of left and right display elements 54*l* and 54*r*, for providing computer-generated stereoscopic left-eye and right-eye images, respectively. A processor 60, which may be a dedicated logic processor, a computer, a workstation, or combination of these types of devices or one or more other types of control logic processing device, provides the computer-generated image data to display elements 54*l* and 54*r*. A pair of cameras 56*l* and 56*r* are mounted on HMD 50 for recording the field of view of the practitioner. These images go to processor 60 for image processing and position detection, as described in more detail subsequently. Additional optional devices may also be provided with HMD 50, such as position and angle detection sensors, audio speakers, microphone, or auxiliary light source, for example. An optional camera 46 is used to detect eye movement of practitioner 12, such as for gaze tracking that can be used to determine where the practitioner's attention is directed.

Figure 6B:
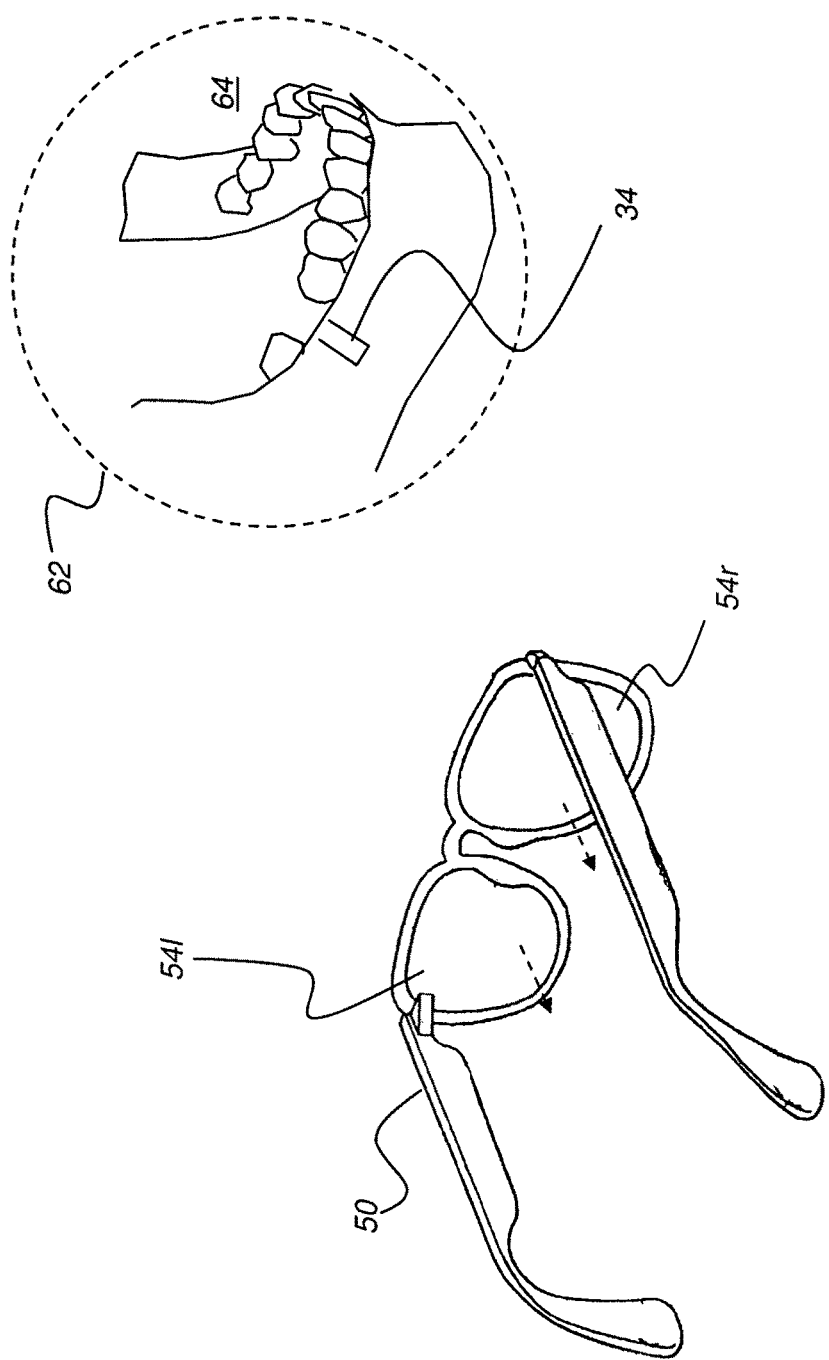
FIG. 6B is a schematic view that shows viewing a computer-generated image in the field of view using a head-mounted device.
Figure 6C:
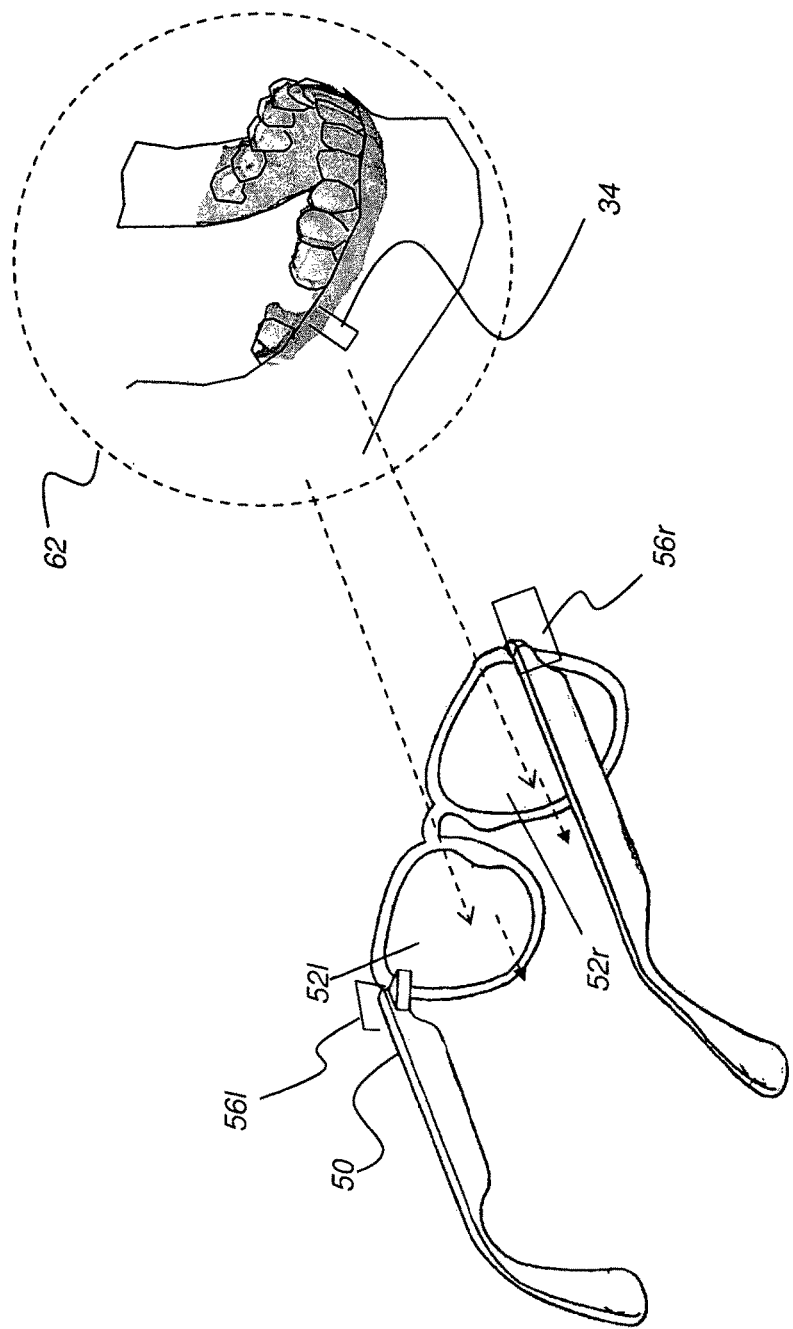
FIG. 6C is a schematic view that shows viewing a computer-generated image superimposed over the field of view using a head-mounted device.

To correlate the obtained CBCT image data with the dentist's view of the patient, and apply this in real-time, HMD 50 performs a number of visualization functions simultaneously. FIGS. 6A, 6B, and 6C show the separate and combined visualization functions that are provided. FIG. 6A represents the actual view of a patient's mouth in a field of view 62 as seen through lenses 52*l* and 52*r*. FIG. 6B shows a computer-generated image 64, as provided from processor 60 and as displayed in stereoscopic form by left and right display elements 54*l* and 54*r*, respectively. By way of example, the position of hole 34 from the implant plan is also shown in the computer-generated image 64. FIG. 6C shows the combined view with the stereoscopic computer-generated image 64 superimposed on the real-world image in field of view 62.

HMD devices and related wearable devices that have cameras, sensors, and other integrated components are known in the art and are described, for example, in U.S. Pat. No. 6,091,546 to Spitzer et al.; U.S. Pat. No. 8,582,209 to Amirparviz; U.S. Pat. No. 8,576,276 to Bar-Zeev et al.; and in U.S. Patent Application Publication 2013/0038510 to Brin et al.

For the superimposition of computer-generated image 64 from CBCT imaging on the real-world view of the patient's mouth, computer-generated image 64 is positionally registered with the view that is detected by cameras 56*l* and 56*r*. Registration can be performed in a number of ways; methods for registration of a computer-generated image to its real-world counterpart are known to those skilled in the arts, including the use of multiple markers and object recognition, for example. According to an embodiment of the present disclosure, a registration sequence is provided, in which the practitioner follows initial procedural instructions for setting up registration coordinates, such as to view the patient from a specified angle to allow registration software to detect features of the patient anatomy. According to an alternate embodiment of the present disclosure, image feature recognition software is used to detect features of the face and mouth of the patient that help to correlate the visual field to the volume image data so that superposition of the virtual and real images is achieved. Image feature recognition software algorithms are well known to those skilled in the image processing arts. According to an embodiment of the present invention, feature recognition software processing uses stored patient image data and is also used to verify patient identification so that the correct information is shown.

Figure 7A:
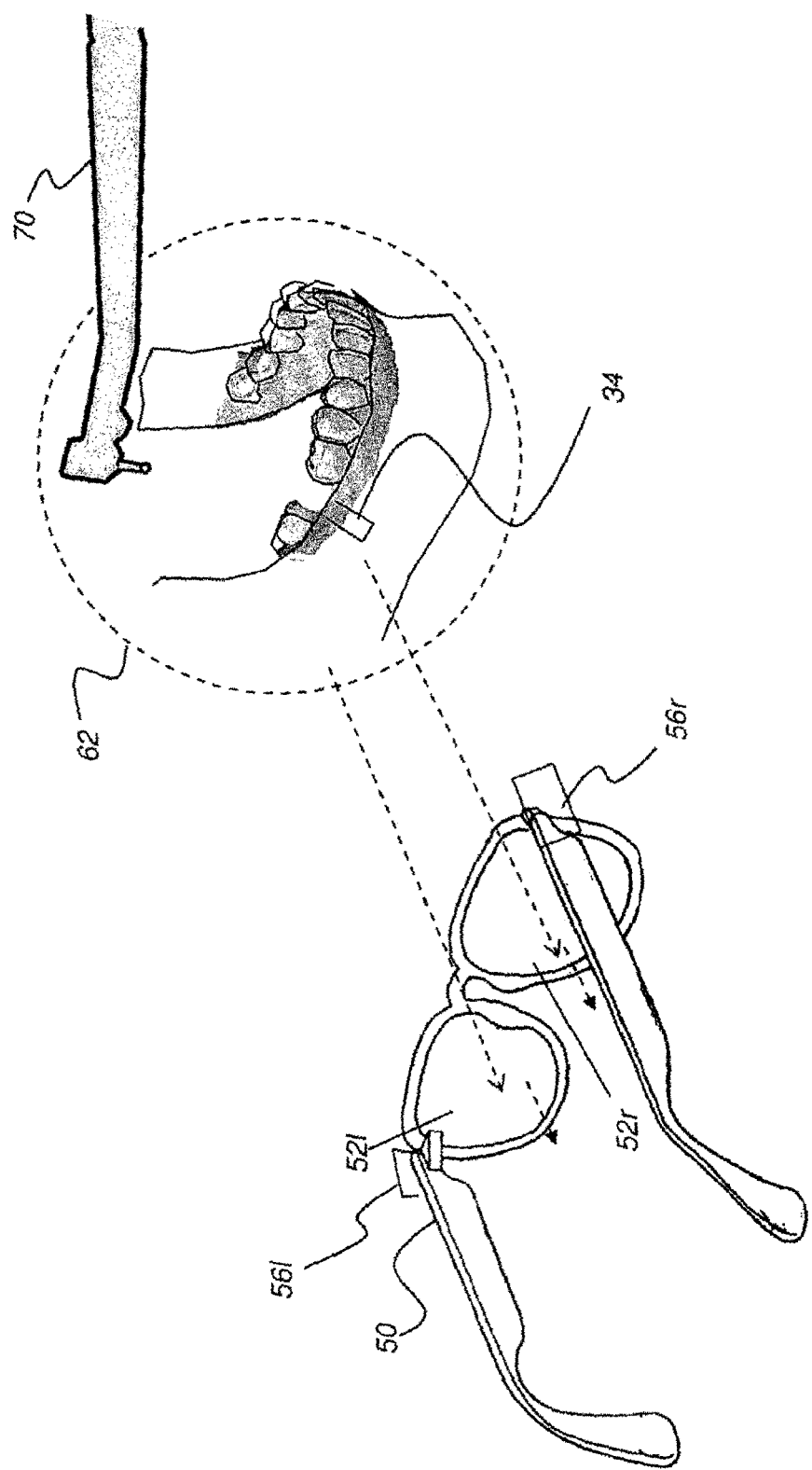
FIG. 7A is a schematic view that shows tracking a dental drill using the head-mounted device.
Figure 7B:
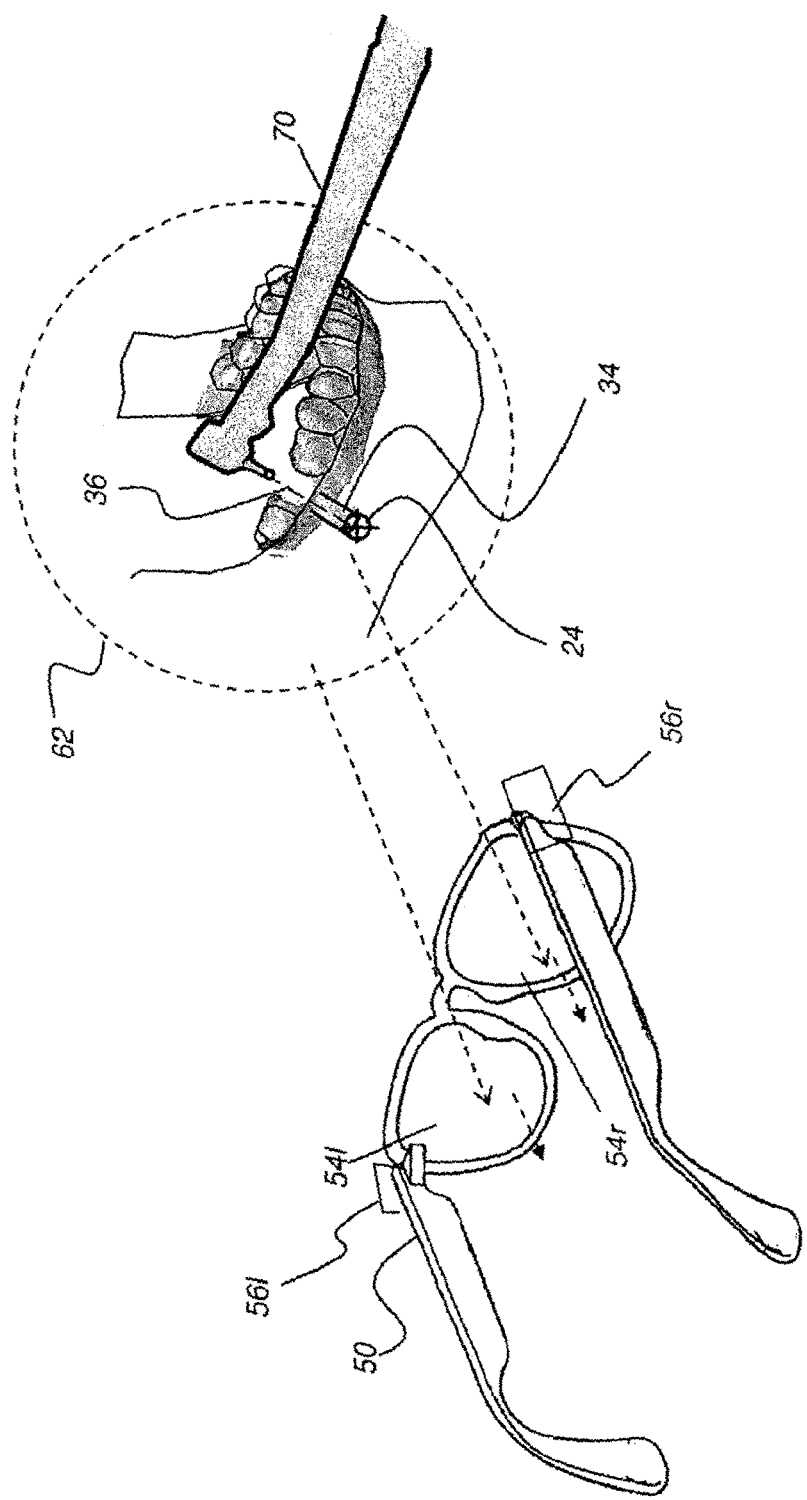
FIG. 7B is a schematic view that shows indicating the drill position, drill axis, and target depth using the head-mounted device.

Once the CBCT computer-generated image 64 is registered with the patient anatomy, proper drill positioning and operation can be displayed to assist the practitioner. As shown in FIG. 7A, cameras 56*l* and 56*r* obtain images of a drill 70 that can be interpreted by processor 60 to determine drill 70 position. Image feature recognition software is used for drill tracking in one embodiment of the present disclosure. As shown in FIG. 7B, highlighting of hole 34 position and a drill axis 36 on the computer-generated image that is displayed by display elements 54*l* and 54*r* can help to guide the practitioner to accurately position and use drill 70 or other tool. Drill guide depth can also be sensed and indicated by a message or by a displayed indicator, such as by highlighting target 24. Display of hole 34 and drill progress using embodiments of the present disclosure can help in reducing or eliminating the need to fabricate drill guides or other custom tools for various types of dental procedures.

Advantageously, the apparatus and method allows interaction between the displayed image content and the position of the dental practitioner and drill or other tool. The computer-generated display is updated as the position of the dentist's head changes relative to the patient and as the positioning of drill 70 changes relative to the hole 34 and target 24.

Detecting drill depth can be performed using any of a number of techniques. According to an embodiment of the present invention, identifiable image features near the drill hole, such as the height of nearby teeth or position of the gumline or jawbone dimensions are used to calculate and monitor drill depth as the hole is being drilled.

The head-mounted device 50 of the present disclosure can be used in any of a number of dental or medical procedures in addition to implant surgery. By providing tools for 3-D visualization of a plan for placement of a device relative to the patient's anatomy using a CBCT scan or other volume image data, then displaying an image based on this data overlaid with the field of view of the practitioner, the method and apparatus of the present disclosure allow the practitioner to carry out steps of a procedure without waiting for fabrication of intermediate guides that are used to direct the drilling of holes in bone structures or the placement of prosthetic devices.

Head mounted devices (HMDs) are known to those skilled in the visualization art and operate by displaying a computer-generated image that correlates to the real-world image that lies in the field of view of an observer, so that the computer-generated image appears to be superimposed on the real-world image. This appearance of superposition can be executed in any of a number of ways. According to an embodiment of the present invention, display elements 54*l* and 54*r* have pixels spaced apart so that the computer-generated image only obstructs a portion of the real-world view and both views are visible at the same time.

According to an alternate embodiment, the computer-generated view is opaque, and the display that appears on display elements 54*l* and 54*r* is rapidly alternated with a clear display through lenses 52*l* and 52*r*, such as 20 times per second or more, so that the appearance of simultaneous viewing is provided to the HMD viewer.

Display elements 54*l* and 54*r* can be devices that incorporate a spatial light modulator, such as a digital micromirror array or similar device, or can be emissive devices, such as organic light-emitting diode (OLED) arrays, for example.

Gaze sensing and other methods can be used to detect head or eye movement for the person wearing the HMD and to report changes to processor 60 so that the displayed stereoscopic images can be adjusted. Gaze sensing can be used, for example, to adjust the view angle for the volume image content.

Figure 8:
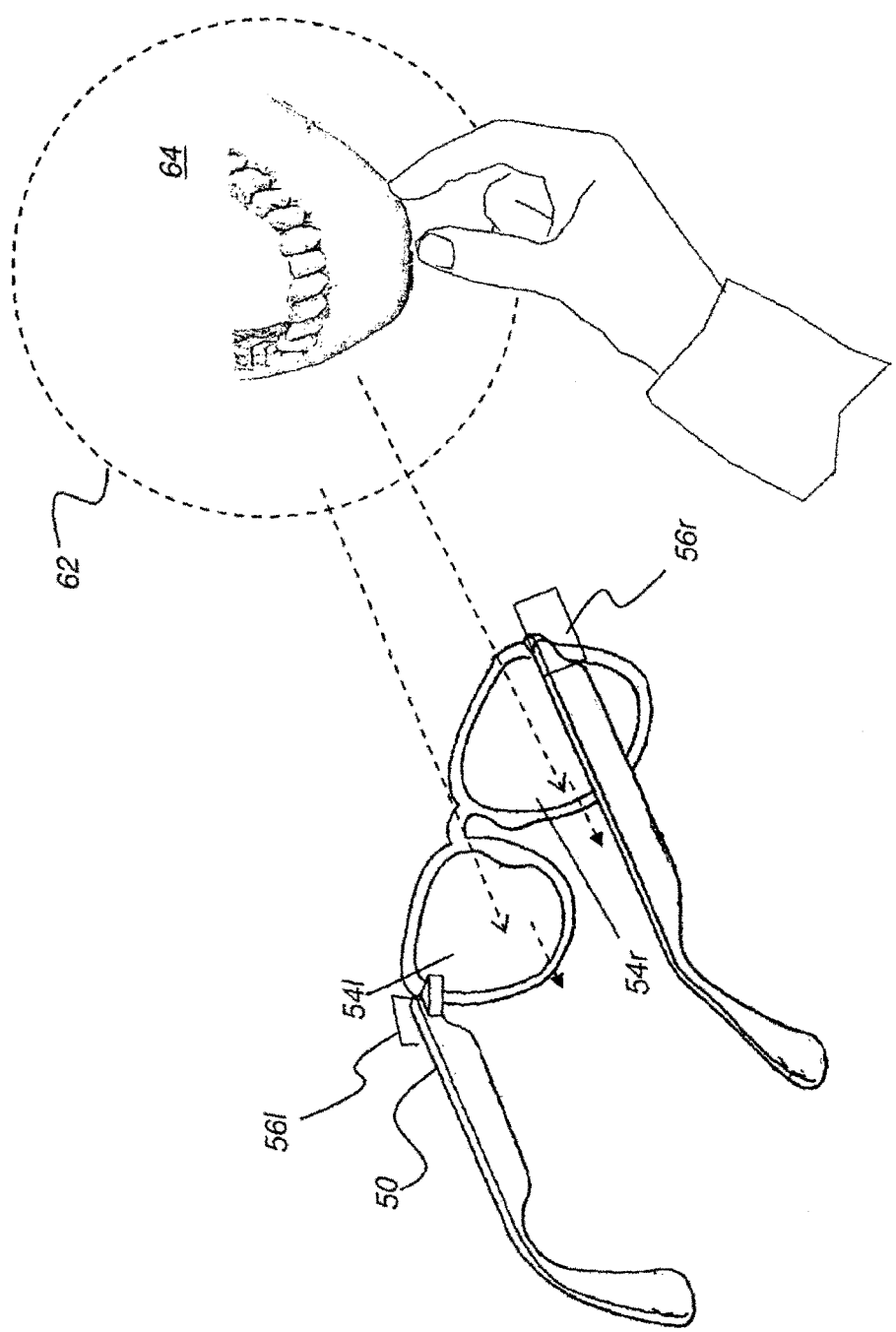
FIG. 8 is a schematic view that shows the head-mounted device in a visualization mode for viewing and manipulating the volume image without reference to the real-world field of view.

In one embodiment, at least a portion of the implant plan is displayed in stereoscopic form on a head-mounted device worn by an observer and tracking patient position so that the displayed portion of the implant plan is registered to the patient anatomy that lies in the observer's field of view. Then, a response to an observer instruction can disable registration of the implant plan to the patient's mouth anatomy and allow changing the view angle of the implant plan. From another aspect, an embodiment also enables a visualization mode that is independent of the real-world field of view. Using this mode, as shown in FIG. 8, the practitioner can examine and manipulate the 3-D volume computer-generated image 64 and change the angle of the implant plan without registration to the patient's mouth. This can be useful, for example, when the practitioner desires an alternate view of an implant site but does not want to move the patient or to move relative to the patient. In the example of FIG. 8, a gestural or audible instruction changes the mode of HMD 50 so that visualization of the 3-D volume image 64 and its manipulation can be carried out regardless of what is actually in the real-world field of view. A subsequent gestural or audible instruction or command then shifts the imaging system back into registration with the view of the patient. Methods for obtaining and interpreting gestural commands are familiar to those skilled in the visualization arts. Thus, one embodiment enables a visualization mode that is independent of the real-world field of view includes disabling the registration of the implant plan to the patient's mouth by a received operator instruction.

Applicants have described a method for guiding the position of a dental drill for implant treatment of a patient, comprising: acquiring a volume image of patient anatomy; superimposing an image of a planned drill hole on a display of the acquired volume image according to observer instructions to form an implant plan; displaying at least a portion of the implant plan in stereoscopic form on a head-mounted device worn by an observer and tracking patient anatomy position and movement so that the displayed portion of the implant plan is registered to the patient anatomy that lies in the observer's field of view; and highlighting the location of the planned drill hole on the head-mounted device display.

The stereoscopic image of the at least a portion of the implant plan can alternate with the real-world view from the head mounted device at least 20 times per second. The volume image can be acquired using cone-beam computed tomography imaging. Displaying the at least a portion of the implant plan on the head-mounted device can include energizing an emissive display device or energizing a spatial light modulator. Highlighting the location of the planned drill hole can include displaying a drill axis. The method can also track the position of the dental drill relative to the highlighted location and indicate, on the display, when the dental drill is in position for drilling the planned drill hole. Tracking the position of the dental drill can include analyzing images from one or more cameras on a head-mounted device and/or providing a message that indicates that the drill has reached a predetermined drill depth.

Embodiments allow the viewer to adjust stereoscopic left-/right-eye separation so that it is more acceptable to the visual characteristics of a particular practitioner. For example, stereo image separation can be widened or narrowed, to provide slightly hyperstereoscopic or hypostereoscopic view conditions, respectively. Separation adjustment can be performed using the operator interface, for example.

According to an alternate embodiment, one or more markers are used as guides to positioning. In addition, visual indicators are provided for assisting in placement and use of the dental drill. Using the sequence shown in FIG. 9, one or more markers are initially positioned in the patient's mouth in a marker positioning step S910. More detailed description of some of the equivalent steps in the FIG. 9 procedure for generating an implant plan 940 are given previously with respect to FIGS. 1 and 2.

Figure 10B:
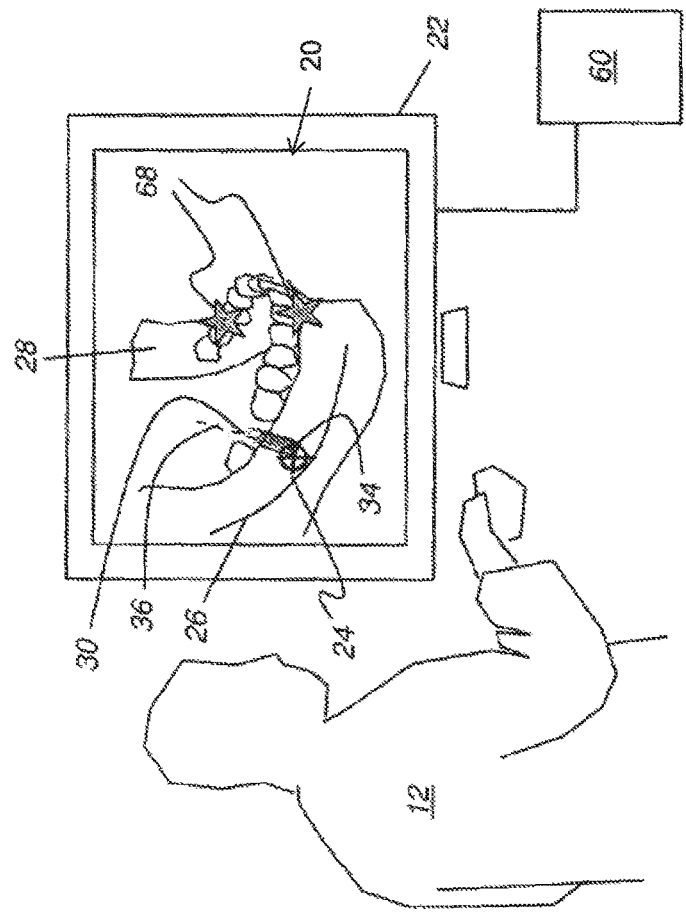
FIG. 10B shows an operator interface for generating an implant plan according to an alternate embodiment of the present disclosure.
Figure 10A:
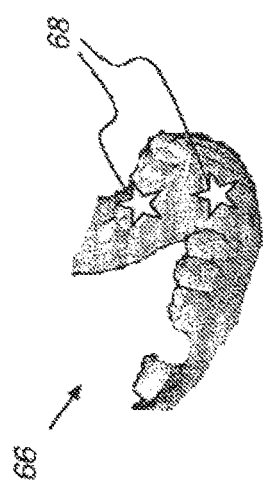
FIG. 10A is a perspective view that shows placement of multiple markers in the patient's jaw.

FIG. 10A is a perspective view that shows placement of multiple markers 68 in a jaw 66 of the patient. Markers 68 can be any type of device suitable for positioning in the patient's mouth without discomfort. Markers 68 are visible, so that they can be detected by a camera using standard image processing techniques. Markers 68 are radio-opaque so that they can be detected in the volume image. Material used for markers 68 include suitable metal or dense ceramic devices that can be clipped or otherwise temporarily coupled to the teeth or jaw. Markers 68 are also selected for visibility, so that image processing logic on processor 60 or other networked processing device can accurately detect markers 68 from camera 56l, 56r images. Markers 68 can have particular spectral characteristics, for example, that distinguish them from teeth and other surrounding structures in the mouth. At least one marker 68 is used.

According to an alternate embodiment, a moire pattern can be displayed and used as a reference marker. The moire pattern is registered to a feature, such as a portion of a tooth or filling, and displays to the viewer wearing head-mounted device 50. The moire pattern is advantaged for stereoscopic viewing, since the appearance of the pattern is dependent on viewing angle. This would allow the use of a single camera, instead of the two cameras that are required for conventional stereoscopic viewing of a marker.

Figure 9:
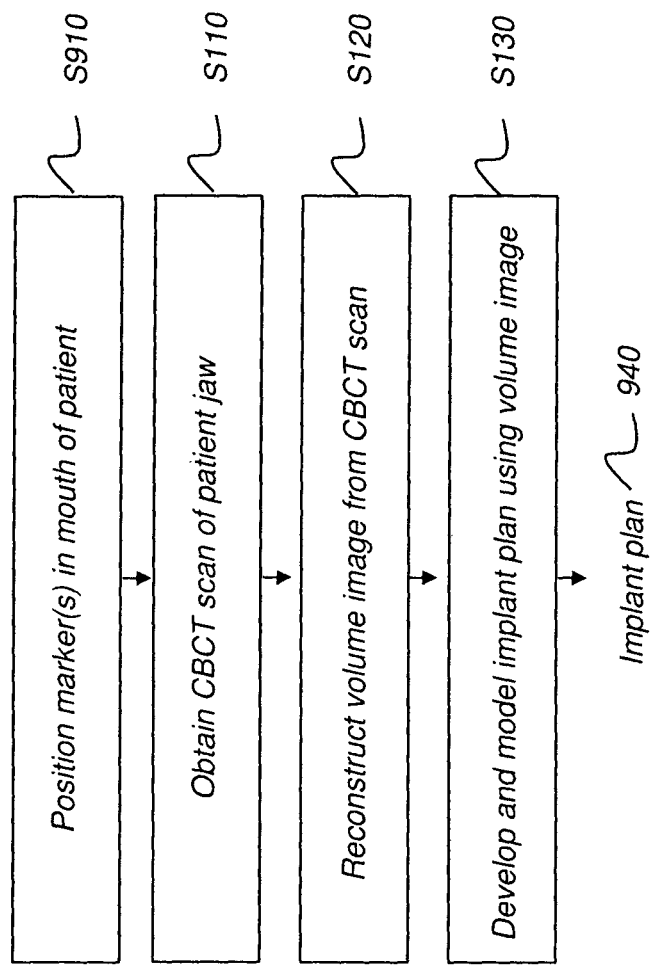
FIG. 9 is a logic flow diagram that gives a sequence of steps for imaging to support implant surgery using augmented visualization with markers.

Continuing with the FIG. 9 sequence, scanning step S110 executes. In scanning step S110, a set of 2-D projection images is acquired, using the scan sequence for CBCT imaging, with 2-D images of the subject obtained from multiple angles relative to the subject. In volume reconstruction step S120, the acquired projection image data is used to generate a reconstructed 3-D volume image. This can be a standard reconstructed volume image formed from a set of 2-D projection images or may be an image generated from combined sets of 2-D projection image data. The reconstructed volume image can be displayed and manipulated, such as by rotation, panning, and other image manipulation utilities that are well known to those skilled in the 3-D volume image display arts.

Continuing with the FIG. 9 sequence, in plan development step S130, an implant plan is developed interactively, by viewing the reconstructed image volume of the jaw at an appropriate angle, modifying the volume image by adding an image that represents an implant or drill tool device to the displayed image, and adjusting the displayed virtual implant or drill tool position within the image of the jaw until the planned implant is accurately modeled. FIG. 10B shows use of operator interface 20 for setting up an implant plan using display 22. Practitioner 12 views volume image 28 of the jaw from an appropriate perspective and identifies the desired location for an implant. The position of markers 68 is shown on the displayed volume image. This position serves as a reference for locating a drill hole 34 for the implant 30 as well as for locating other features in the volume image 28, such as facial nerve 26 and one or more targets 24, such as the location of the top or bottom of the drill hole 34 for the implant, or central axis 36 for drilling the hole. Operator interface 20 alternately displays a visualization of implant 30 in a 3-D view on the displayed volume image 28.

At the conclusion of step S130, implant plan 940 is formed, in which an image representing the implant or drill hole for the implant is registered within the volume image for the patient's jaw or corresponding portion of the patient's jaw to provide a virtual view that can be controlled and manipulated in 3-D space. Implant plan 940 includes reference positioning information that is inherently obtained from the positioning of markers 68. Implant plan 940 can include additional metadata supporting the image data, with information about the patient, data on relative bone density, implant material type, hole diameter and depth, and other information.

Figure 11:
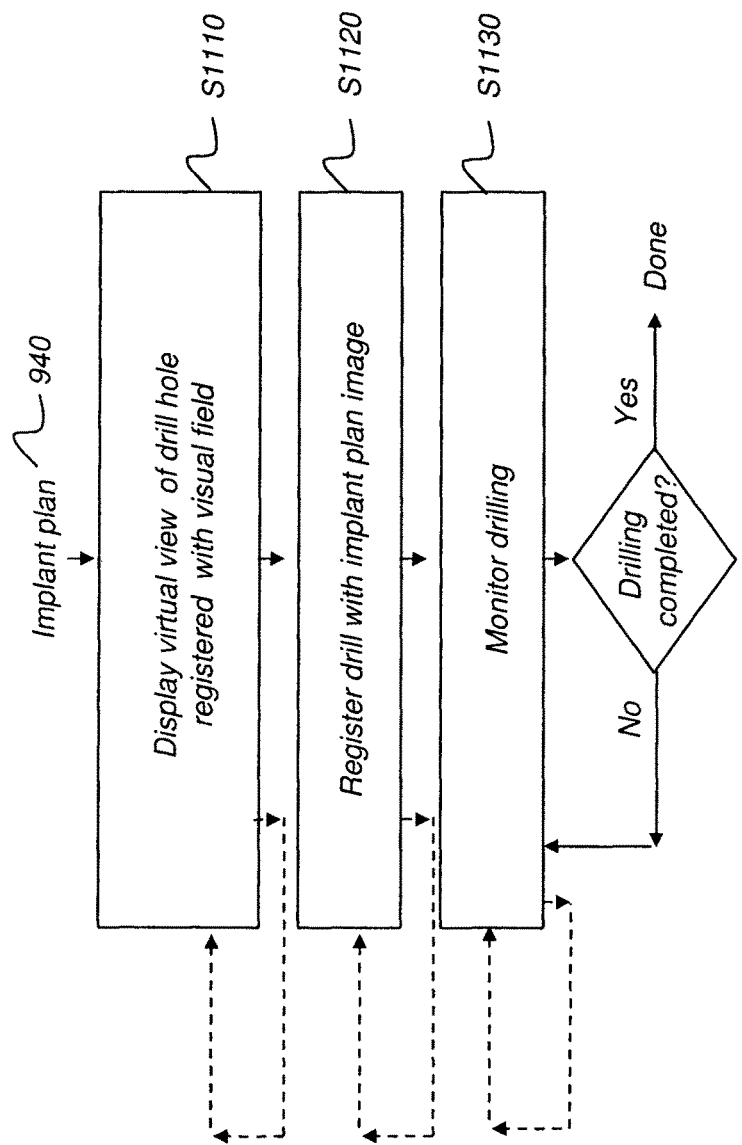
FIG. 11 is a logic flow diagram that shows steps for using a 3-D implant plan in surgery.

The logic flow diagram of FIG. 11 shows the steps for surgery once the implant plan 940 has been generated. As described in FIGS. 5 through 8, visualization apparatus, such as head-mounted device 50, is worn by the practitioner during surgery. Head-mounted device 50 enables the drill hole 34 location to be identified and displayed in register with the corresponding jaw and teeth of the patient who is seated in the treatment chair and is in the visual field of the observer.

In the FIG. 11 sequence, a visualization step S1110 is executed by imaging system 100, in which the view of the patient that has been obtained from cameras 56l and 56r on head-mounted device 50 is used to determine the orientation and position of the patient's mouth within the observer's visual field. The image of at least drill hole 34 (FIG. 10B) is projected or otherwise displayed from the head-mounted device 50. Stereoscopic rendering gives the displayed image content, drill hole 34 in this example, the appearance of being in position within the mouth of the patient. Markers 68 that were positioned in the patient's mouth as described previously with reference to FIGS. 9 and 10A provide a set of reference 3-D coordinates that help to locate spatial position and orientation with a measure of accuracy.

As is represented by the dashed lines shown for step S1110 in FIG. 11, the displayed virtual view is refreshed regularly to adjust view angle and to correct for misregistration. Using markers 68, for example, a change in relative position of markers 68 indicates the need to recalculate position, size, and orientation of the drill hole 34 rendering. This helps to compensate for unavoidable movement by either or both the patient and the practitioner during surgery.

A drill registration step S1120, which can be executed simultaneously with step S1110, registers the actual drill that is held by the dentist with the planned drill hole 34 and related image content specified in implant plan 940. To do this, the visualization apparatus used by the practitioner detects the position of the drill in the dentist's hand and tracks this position relative to the intended drill position in implant plan 940. A number of indicators suggestive of drill movement can be displayed, appearing within the field of view of the practitioner, as described subsequently.

Figure 12:
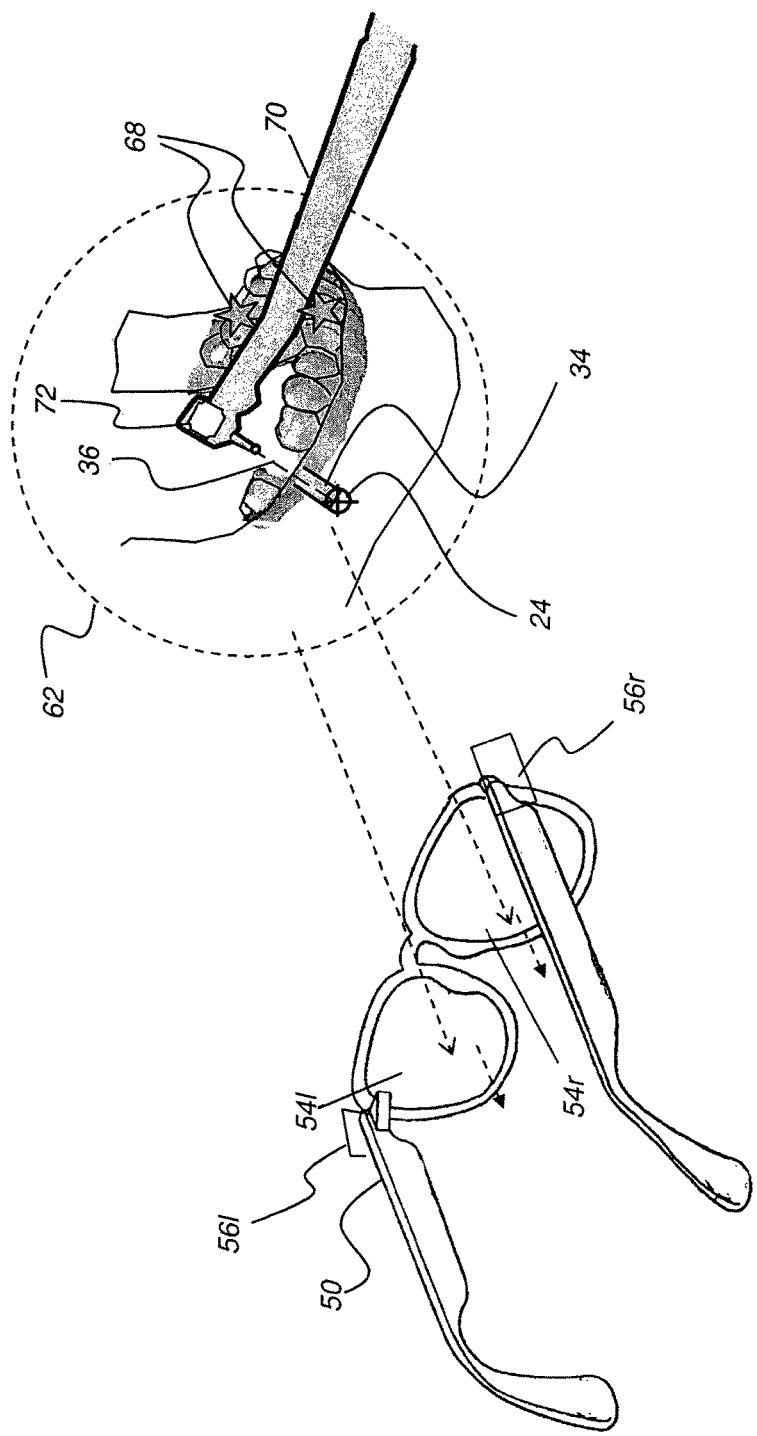
FIG. 12 is a perspective view that shows placement of markers on the dental drill and in the mouth of the patient.

According to an alternate embodiment, as shown in FIG. 12, drill 70 is also provided with one or more markers 72. Position-sensing and calculation logic executing on host processor 60 uses marker(s) 72 in conjunction with marker(s) 68 for guiding the observer to move drill 70 into position.

As represented by the dashed lines shown in FIG. 11, the view showing drill registration is refreshed regularly to adjust registration and compensate for unavoidable movement by either or both the patient and the practitioner. A drill monitoring step S1130 continues to track drill progress in an ongoing manner once the drill is in position and indicates when the drilling operation is done and this phase of the surgery completed. Step S1130 includes a periodic refresh cycle.

Figure 13A:
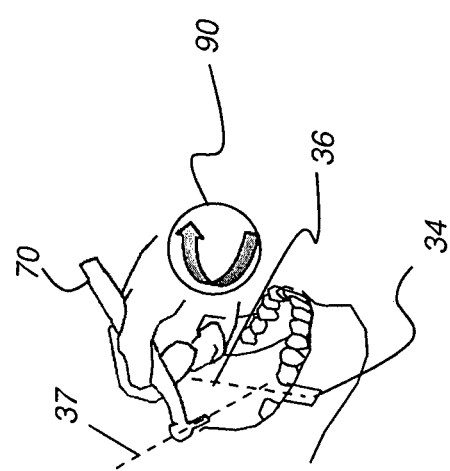
FIGS. 13A, 13B, 13C, and 13D show various types of indicators that can display to the observer in stereoscopic imaging mode for guiding the drill operation.

FIGS. 13A, 13B, 13C, and 13D show various types of indicators 90, 92, 94, 96, and 98 that display as "virtual" indicators from HMD 50 in order to help guide drill positioning and operation. In FIG. 13A, indicator 90 is a circular icon with an arrow that indicates the needed movement of drill 70 to align a tool axis 37 with drill axis 36 at hole 34. Indicator 90 rotates to show preferred movement direction and changes its color and intensity as drill 70 is moved nearer to the desired position. According to an embodiment, indicator 90 displays in the field of view of the observer at a variable intensity, based on the relative need for adjustment, then fades as the desired position is attained.

Figure 13B:
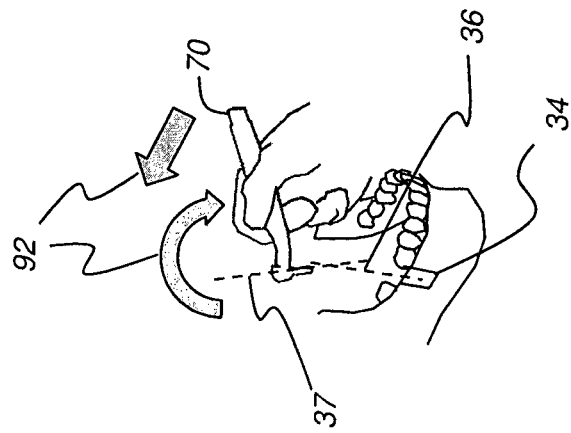

FIG. 13B shows indicators 92 as arrows that are displayed for directing the positioning of drill 70. Indicators 92 appear above the hand of the practitioner holding drill 70, reducing visual obstruction while still providing positioning assistance.

Figure 13D:
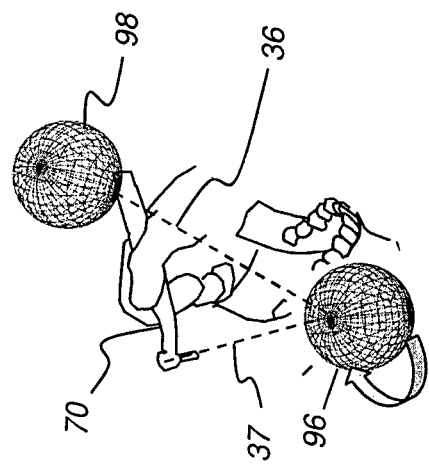
Figure 13C:
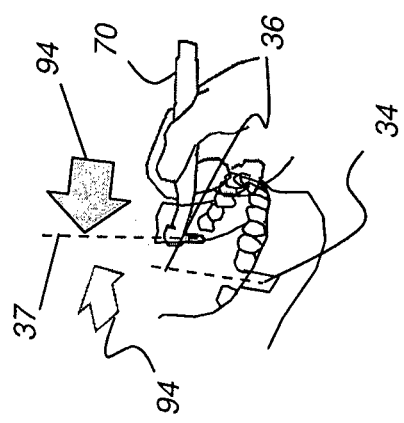

FIG. 13C shows indicators 94 in an alternate embodiment. Arrows are used as indicators 94, with one arrow highlighted at a time. Highlighting, that is, displaying with a more pronounced brightness, can be used to indicate in which direction more movement is needed.

FIG. 13D shows indicators 96 and 98 that have stereoscopic appearance. In the example shown, indicator 96 indicates the orientation and position of the tool axis 37. Indicator 98 indicates the orientation and position of drill axis 36. Color or other highlighting is used to indicate misalignment. When alignment is correct, indicators 96 and 98 fade or disappear.

Other options for stereoscopic indicators include indicators that utilize visual patterns that are responsive to the relative accuracy of positioning and alignment. Moire patterns, for example, can be advantaged because they can have stereoscopic effects, without requiring stereoscopic image generation.

As a form of highlighting, indicators can change state, such as changing color, flashing, or sending out some other visible sign when drilling has been completed or when an error or problem has been detected.

According to an alternate embodiment, a marker 72, optionally positioned on the drill as shown in FIG. 12, is used to help indicate drill depth. Drill depth can be calculated based on the relative position of marker 72 to markers 68. Drill depth can be calculated from the implant plan according to relative position of bone and nerve structures, as described previously.

Accordingly to at least one embodiment, the system utilizes a computer program with stored instructions that perform on image data that is accessed from an electronic memory. As can be appreciated by those skilled in the image processing arts, a computer program of an embodiment of the present disclosure can be utilized by a suitable, general-purpose computer system, such as a personal computer or workstation. However, many other types of computer systems can be used to execute the computer program of the present disclosure, including an arrangement of networked processors, for example. The computer program for performing the method of the present disclosure may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

What is claimed is:

1. A method for drill placement for a dental drill procedure for implant treatment of a patient, comprising:
acquiring a volume image of patient dentition anatomy;
superimposing an image of a planned drill hole on a display of the acquired volume image according to observer instructions to form an implant plan;
displaying at least a portion of the implant plan in stereoscopic form on a head-mounted device worn by the observer along with a real-world view from the head mounted device and tracking patient position so that the displayed portion of the implant plan is registered to the patient dentition anatomy that lies in the observer's field of view and at least a portion of the implant plan is superimposed on the real-world view on the patient dentition anatomy in the observer's field of view;
highlighting the location of the planned drill hole on the head-mounted device display; and
tracking the position of the dental drill for comparison to the highlighted location, further comprising
disabling the registration of the implant plan to the patient dentition anatomy in response to a received instruction,
manipulating the acquired volume image to change one or more of a drill hole angle, a drill hole depth, or a drill hole location of the unregistered implant plan, and
receiving a subsequent instruction to shift the changed implant plan back into registration to the patient dentition anatomy in the observer's field of view.

2. The method of claim 1 wherein a display of the stereoscopic image of the at least a portion of the implant plan from the head mounted device alternates with a display of the real-world view from the head mounted device at least 20 times per second.

3. The method of claim 1 further comprising providing a message that indicates that the drill has reached a predetermined drill depth, wherein displaying the at least a portion of the implant plan on the head-mounted device comprises projecting the implant plan superimposed on the patient dentition anatomy.

4. The method of claim 1 wherein highlighting the location of the planned drill hole further comprises displaying a drill axis.

5. The method of claim 1 further comprising indicating, on the display, when the dental drill is in position for drilling the planned drill hole, wherein tracking the position of the dental drill comprises analyzing images from one or more cameras on the head-mounted device.

6. The method of claim 1 further comprising changing the stereoscopic display in accordance with a change in a field of view of the observer through the head-mounted device.

7. The method of claim 1 wherein the displayed portion of the implant plan comprises one or more markers.

8. The method of claim 1 further comprising displaying an indicator in the observer's field of view from the head-mounted device, wherein the indicator's appearance relates to one or more of the relative distance of the dental drill to the displayed drill hole, the angle of the dental drill relative to the displayed drill hole, and the relative depth of the drill hole, wherein the displayed indicator indicates a recommended change in the positioning of the dental drill.

9. The method of claim 8, wherein tracking patient mouth anatomy comprises tracking the visible marker, wherein the marker is radio-opaque, wherein the marker is a first marker and wherein there is a second marker coupled to the dental drill, wherein the displayed indicator appears near the drill in the display from the head-mounted device, wherein the displayed indicator is a moiré pattern that is patterned to change its appearance according to the angle at which it is viewed, wherein the displayed indicator indicates a recommended change in the positioning of the dental drill.

10. The method of claim 9 wherein the visible marker is a first visible marker and further comprising at least a second visible marker in the mouth of the patient and wherein the first and at least the second visible markers are used to locate the planned drill hole of the implant plan.

11. The method of claim 1 further comprising changing the display of the image of the planned drill hole according to the position of the observer relative to the patient's mouth.

12. The method of claim 1 wherein the separation distance between a left-eye and a right-eye image in the stereoscopic display is adjustable by the observer.

13. A dental imaging apparatus, comprising:
a computerized tomography scanning apparatus that obtains a volume image of a patient from a plurality of two-dimensional images taken at different angles relative to the patient;
a host processor that is in signal communication with the computerized tomography scanning apparatus and that is adapted to generate the volume image from the plurality of two-dimensional images;
a first display that is in signal communication with the host processor and that provides an operator interface that is adapted to display positioning of at least a drill hole relative to the volume image; and
a second display of a head mounted device that is in signal communication with the host processor, wherein the second display is worn by an observer and further comprises at least a first camera that is adapted to acquire an image of the visual field of the observer, the second display enabling viewing at least a portion in stereoscopic form on a head-mounted device worn by the observer along with a real-world view from the head mounted device and tracking patient position so that the displayed portion of the implant plan is registered to the patient dentition anatomy that lies in the observer's field of view and at least a portion of the implant plan is superimposed on the real-world view on the patient dentition anatomy in the observer's field of view, where the location of the planned drill hole is highlighted on the second display, and
the second display enabling displaying an indicator in the observer's field of view from the head-mounted device, wherein the indicator's appearance relates to one or more of the relative distance of the dental drill to the displayed drill hole, the angle of the dental drill relative to the displayed drill hole, and the relative depth of the drill hole, wherein the displayed indicator indicates a recommended change in the positioning of the dental drill, wherein tracking patient mouth anatomy comprises tracking the visible marker, wherein the marker is radio-opaque, wherein the marker is a first marker and wherein there is a second marker coupled to the dental drill, wherein the displayed indicator appears near the drill in the display from the head-mounted device, wherein the displayed indicator is a moiré pattern that is patterned to change its appearance according to the angle at which it is viewed, wherein the displayed indicator indicates a recommended change in the positioning of the dental drill.

14. A method for drill placement for a dental drill procedure for implant treatment of a patient, comprising:
acquiring a volume image of patient dentition anatomy;
superimposing an image of a planned drill hole on a display of the acquired volume image according to observer instructions to form an implant plan;
displaying at least a portion of the implant plan in stereoscopic form on a head-mounted device worn by the observer along with a real-world view from the head mounted device and tracking patient position so that the displayed portion of the implant plan is registered to the patient dentition anatomy that lies in the observer's field of view and at least a portion of the implant plan is superimposed on the real-world view in the observer's field of view; and
highlighting the location of the planned drill hole on the head-mounted device display, the method further comprising
displaying an indicator in the observer's field of view from the head-mounted device, wherein the indicator's appearance relates to one or more of the relative distance of the dental drill to the displayed drill hole, the angle of the dental drill relative to the displayed drill hole, and the relative depth of the drill hole, wherein the displayed indicator indicates a recommended change in the positioning of the dental drill, wherein tracking patient mouth anatomy comprises tracking the visible marker, wherein the marker is radio-opaque, wherein the marker is a first marker and wherein there is a second marker coupled to the dental drill, wherein the displayed indicator appears near the drill in the display from the head-mounted device, wherein the displayed indicator is a moiré pattern that is patterned to change its appearance according to the angle at which it is viewed, wherein the displayed indicator indicates a recommended change in the positioning of the dental drill.

15. The method of claim 14 further comprising disabling the registration of the implant plan to the patient-dentition anatomy in response to a received instruction, manipulating the acquired volume image to change one or more of a drill hole, a drill hole depth, or a drill hole location of the unregistered implant plan, and receiving a subsequent instruction to shift the changed implant plan back into registration to the patient-dentition anatomy in the observers field of view.

* * * * *